(12) United States Patent
Zhong et al.

(10) Patent No.: US 8,080,139 B2
(45) Date of Patent: Dec. 20, 2011

(54) METHOD OF ANHYDROUS ETHANOL PRODUCTION USING CIRCULATION BY MULTIPLE TOWERS ALTERNATION

(75) Inventors: Yaling Zhong, Sichuan (CN); Yuming Zhong, Sichuan (CN)

(73) Assignee: Yaling Zhong, Sichuan (CN)

( * ) Notice: Subject to any disclaimer, the term of this patent is extended or adjusted under 35 U.S.C. 154(b) by 795 days.

(21) Appl. No.: 12/065,485

(22) PCT Filed: Aug. 29, 2006

(86) PCT No.: PCT/CN2006/002222
§ 371 (c)(1),
(2), (4) Date: Jun. 6, 2008

(87) PCT Pub. No.: WO2007/025472
PCT Pub. Date: Mar. 8, 2007

(65) Prior Publication Data
US 2008/0245653 A1    Oct. 9, 2008

(30) Foreign Application Priority Data

Sep. 2, 2005   (CN) .......................... 2005 1 0098533

(51) Int. Cl.
  B01D 3/38    (2006.01)
  B01D 15/00   (2006.01)
  C07C 29/76   (2006.01)
  C07C 29/80   (2006.01)
  C07C 31/08   (2006.01)
  C12G 3/14    (2006.01)

(52) U.S. Cl. .................. 203/19; 95/96; 95/902; 203/41; 203/96; 203/DIG. 13; 210/694; 210/741; 210/774; 210/806; 210/808; 426/493; 568/916; 568/917

(58) Field of Classification Search ................ 203/3, 19, 203/41, 96, DIG. 7, DIG. 13; 210/664, 694, 210/712, 741, 774, 805–808; 95/96, 902; 426/465, 493, 494; 568/916, 917
See application file for complete search history.

(56) References Cited

U.S. PATENT DOCUMENTS

| 4,273,621 A | * | 6/1981 | Fornoff ........................... 203/19 |
| 4,373,935 A | * | 2/1983 | Ausikaitis et al. .............. 95/123 |
| 4,407,662 A |   | 10/1983 | Ginder |
| 4,465,875 A |   | 8/1984 | Greenbank et al. |
| 4,487,614 A | * | 12/1984 | Yon ................................. 95/93 |
| 4,612,405 A | * | 9/1986 | McCaffrey et al. ........... 568/916 |

FOREIGN PATENT DOCUMENTS

| CN | ZL 88102169 | 11/1989 |
| CN | 1328987 A | 1/2002 |
| CN | 1348942 A | 5/2002 |
| CN | 1498678 A | 5/2004 |

* cited by examiner

*Primary Examiner* — Virginia Manoharan
(74) *Attorney, Agent, or Firm* — Volpe and Koenig, P.C.

(57) ABSTRACT

The present invention relates to a method of anhydrous ethanol production using circulation by multiple towers' alternation, the procedure includes the steps of heating, adsorption, internal circulation, vacuum suction, washing and resolving etc. The method can prolong the life of adsorbent, reduce the heat exchanger's surface, cooling water, the equipment investment and energy consumption, provide high ethanol recovery rate and high dehydration, and protect environment.

4 Claims, 1 Drawing Sheet

METHOD OF ANHYDROUS ETHANOL PRODUCTION USING CIRCULATION BY MULTIPLE TOWERS ALTERNATION

This application is a 35 USC 371 national phase application of PCT/CN2006/002222.

FIELD OF INVENTION

This invention relates to a method of anhydrous ethanol production, especially refers to a method of anhydrous ethanol production using internal circulation by multiple towers' alternation.

BACKGROUND

As an important industrial chemical and solvent, anhydrous ethanol plays an immeasurable role in national economy. With the rapid growth of market demand and continuous improvement of product quality needs, the methods of anhydrous ethanol production are constantly improving and developing. Preparation methods of anhydrous ethanol are traditional calcium oxide and ion exchange technique at the earliest, benzene azeotropic distillation technique, pentane azeotropic technique, extractive distillation technique, molecular sieve technique etc. Though azeotropic distillation technique and extractive distillation technique can produce high-concentrated ethanol, these methods inevitably have the trace of Organic dissolved impurities, moreover with big investment, high consumption, low rate relatively.

Adsorption method by using adsorbent has been industrialized since the 1980s with a new alcohol dehydration technology. Adsorbents are activated carbon, silica gel, activated alumina, molecular sieve, cereal powder and so on. Among them molecular sieve adsorption have the best capacity and selectivity. Meanwhile it has good thermal stability and fine mechanical performance, with no swelling after adsorption and no ravel because of wet. The adsorbent has a long life, up to 5-7 years. Therefore this technology has been widely applied.

ZL 88102169, CN 1498678 (application number is 02150135.1), CN 1328987A (application number is 01118051.X), U.S. Pat. No. 4,465,875, U.S. Pat. No. 4,407,662 and other patents relate to anhydrous ethanol production by adsorption. However, the feed method nowadays is feeding from below, which cause the gas stir up and the layer of adsorption bed displace. The product often carries over adsorbent, which influence the life of adsorbent. Meanwhile In the production of anhydrous ethanol, cooling water costs a lot because of steam generation and cooling process. In addition, when desorbed gas cool down instantaneously, the usage of cooling water and heat exchange surface area are great because of focused desorption, which cause large equipment loading, great energy, great investment in equipment and high operating costs. In the course of desorption, the valve is opened and closed directly, which makes gas generate momentum. And it can easily cause adsorbent pulverization. The instantaneous heat is great, and the heat exchange surface area is large in unit time.

SUMMARY

The invention aims to solve the shortcomings of existing technology, and offer a method of anhydrous ethanol production using internal circulation by multiple towers' alternation with small equipment loading, low equipment investment, and low consumption, and long life of adsorbent.

To achieve the above objectives, a method of anhydrous ethanol production using internal circulation by multiple towers' alternation comprising the procedures as follows is provided:

1. 70-99 wt % ethanol aqueous solution, as raw material, passes a heat interchanger and then enters a vaporizer for heating and vaporization by steam, and is heated to 80-220° C.;

2. the heated vapor stream of raw material alternatively enters several adsorption towers (at adsorption mode) in turn from the top thereof for adsorption and dehydration, the pressure is 0.1-2.5 Mpa and the adsorption process lasts for 50-500 seconds; when the water concentrations in any one of the adsorption towers is nearly saturated, the feed to the adsorption tower is stopped; ethanol stream flows out from the bottom of the adsorption tower and enters the heat interchanger to heat the raw ethanol, and after being cooled down by a product cooler, the ethanol product is sampled, and the qualified product containing 99.5-99.99 wt % ethanol enters a product storage tank, while the unqualified product is sent to a raw ethanol tank for re-processing;

3. after adsorption and dehydration, the valve is regulated to allow alcohol in the tower gradually to flow into those towers at adsorption mode until their pressures are equal, then internal circulation is established, it is the internal circulation is the course of balancing the pressure in the two towers;

4. after internal circulation and pressure being balanced, the top of the adsorption tower is communicated with a vacuum system to suck out the remaining of the ethanol fluid which is liquefied after mixing with ejecting recycling liquid and becomes a new recycling liquid to be sent to a recycle pump, part of the recycling liquid (light wine) is sent to a light wine rectifying tower and collected in a raw ethanol tank as raw material after rectification, and the liquid in the bottom of the rectifying tower is pollution-free waste water which can be discharged directly, and the remaining recycling liquid enters the ejector again as ejecting liquid;

5. then dry alcohol from the adsorption tower, which is in the state of adsorption, is used to flow through the molecular sieve in the vacuum tower from the top to regenerate the molecular sieve after desorption;

6. the pressure of the tower after regeneration is −0.01-0.1 MPa, which could be regarded as vacuum, and is then connected to another adsorption tower in which adsorption has been completed, to form an internal circulation, and increase the pressure, then it reaches a plateau, and enters the second operation process.

Advantages of this Method:

1. Feeding from top can solve the problem of displacement of the adsorption bed layers and the problem that the adsorbent is often carried by the product, so that the life of adsorbent can be prolonged.

2. By adopting the way of internal circulation by multiple towers' alternation in this method, instead of carrying out desorption after all adsorption, but carrying out the adsorption, desorption and washing alternatively, the instantaneous pulse heat in the process can be reduced. Furthermore, the desorption gas and washing gas are condensed alternatively, which can reduce the surface area of the heat exchanger and the usage of cooling water.

3. In production process, the desorbed gas from the adsorption tower, as a feed gas, enters another tower (at adsorption mode) and makes an internal circulation, which reduces the workload of the device and the cost of energy.

4. In production process, for the desorbed gas from the adsorption tower, other methods are to recycle after cooling down; while this method is to suck out by vacuum draw and to mix with recycling liquid from the ejector and then turn to liquid phase from gas phase, meanwhile to use the liquefied materials as the source of the ejector, which makes good use of heat, reduces the equipment investment and reduces energy consumption.

5. This method adopts advanced automatic control means, using a method of anhydrous ethanol production using internal circulation by multiple towers' alternation in the process, which can automatically achieve consecutive dehydration and reproduction. This method has no pollution, low energy consumption, low running costs, short flow, low investment, long life, high ethanol recovery rate and high dehydration.

6. In this method the valves are regulating valves, which can reduce pressure and obtain gradual desorption, decrease the release heat in unit time, reduce the surface area of the heat exchanger, and save the investment by regulation. Meanwhile, without impulse force of gas caused by valves opening directly like other methods, the life of catalyst can be effectively increased.

7. This method provides high dehydration, which can reach up to 99.99%. Meanwhile it can adjust the degree of dehydration of the dehydrate ethanol as requested.

DETAILED DESCRIPTION OF THE PREFERRED EMBODIMENTS

Case 1

Figure 1:
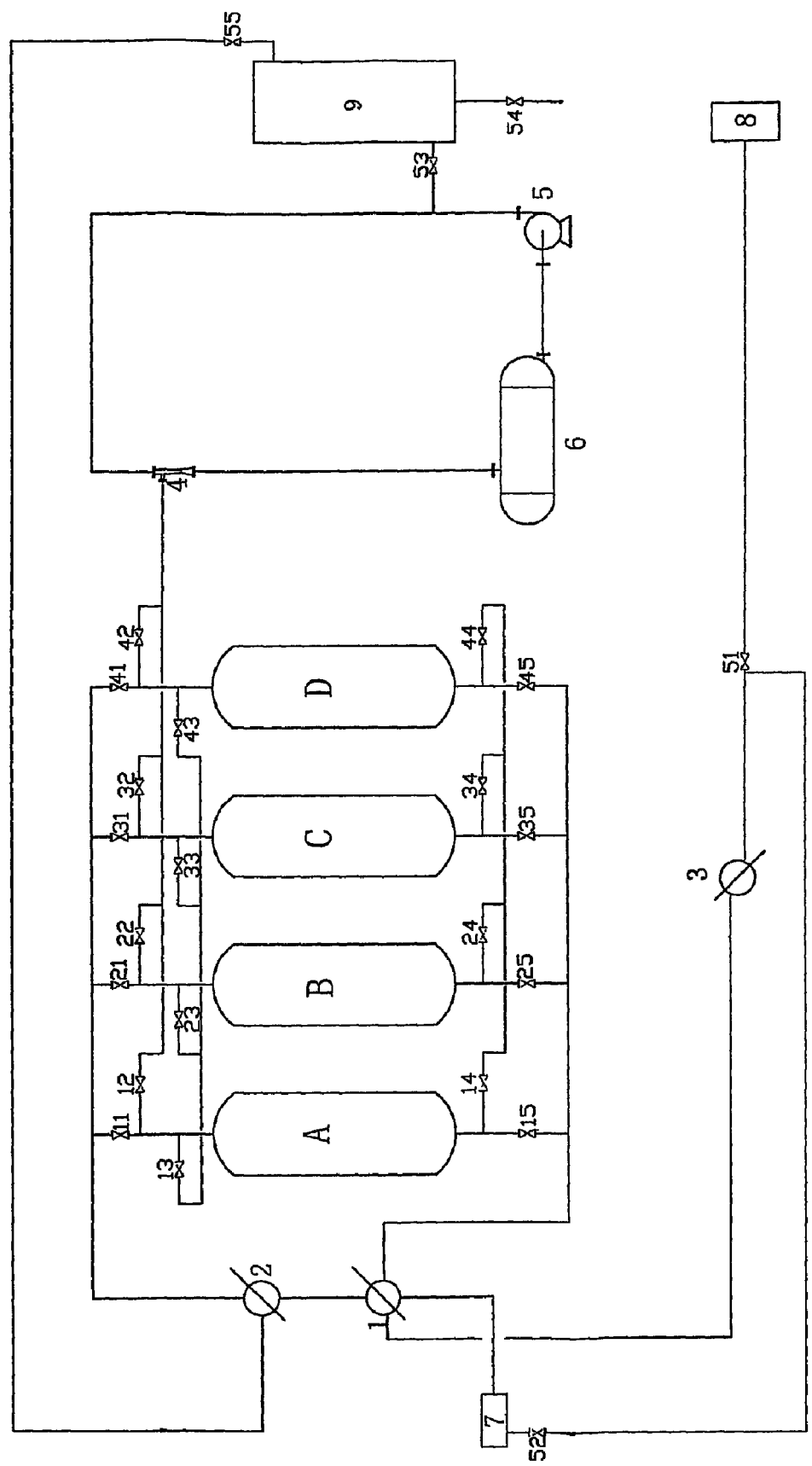
FIG. 1 is a flowchart of the method of anhydrous ethanol production using internal circulation by multiple towers' alternation provided by the present invention.

Refer to FIG. 1, about 70 wt % ethanol aqueous solution, as raw material, passes a heat interchanger 1 and then enters a vaporizer 2 for heating and vaporizing by steam, and is heated to 80° C. The heated vapor stream of raw material enters an adsorption tower A from top to bottom through a valve 11. At that time valves 12, 13, 14 and 15 are closed. The adsorption process lasts for 250 seconds. And the heated vapor stream enters adsorption tower B from top to bottom through a valve 21. At that time valves 22, 23, 24 and 25 are closed. The pressure in tower A and B is set at 0.1 Mpa. And the adsorption hour is 500 seconds. Ethanol vapor flows out through valves 15 and 25 from the bottom of the tower. Then it enters the heat interchanger 1 to heat raw ethanol and passes through a cooler 3. After being cooled down, the ethanol product is sampled, and the qualified product containing 99.5 wt % ethanol enters a product storage tank 8 through a valve 51. The unqualified product shall be sent to raw ethanol tank through a valve 52 for re-processing.

After adsorption and dehydration in the adsorption tower A, the valves 13 and 43 are regulated to allow the remaining ethanol vapor gradually flow to the top of tower D through valves 13 and 43. At that time valves 11, 12, 14, 15, 41, 42, 44 and 45 are closed, until the pressures of tower A and tower D are equal, and then an internal circulation is established. In that process, some ethanol vapor is high-concentrated, so it does not have to be pre-processed but enters the tower for adsorption directly. In that case, it can improve the thermal efficiency and reduce the equipment investment.

After internal circulation and pressure being balanced, the top of tower A is communicated with a vacuum system 4. Ethanol vapor is sucked out by vacuum draw. A valve 31 of an adsorption tower C is open so as to let the heated ethanol vapor in. Valves 32, 33, 34, 35 are closed. The pressure of the adsorption tower C is 2.5 Mpa, and the adsorption hour is set at 500 seconds. The remaining of the ethanol vapor in tower A is sucked out by vacuum draw and mixed with the ejecting recycling liquid. After entering recycling liquid tank 6, it turns to a new recycling liquid and is sent into a recycling pump 5. While part of the recycling liquid is sent to a rectifying tower 9 through a valve 53, and enters a vaporizer 2 through a valve 55 after rectifying, and is then superheated it as raw ethanol vapor. The bottoms of the rectifying towers collect pollution-free wastewater. It can be discharged from a valve 54, while the other enters the ejector again as ejecting liquid. The recycling liquid as above-mentioned is ethanol aqueous solution.

Then the dry alcohol from the tower C, which is in a state of adsorption, is used to flow through the molecular sieve in the vacuum tower A from the top to regenerate the molecular sieve after desorption. At that time, valves 33 and 13 are open, while valves 31,32,34,35, 11, 12, 14 and 15 are closed.

Then the pressure of tower A is −0.01 Mpa after regeneration. Connect it to the adsorption tower B in which adsorption has finished, to form an internal circulation, and then increase the pressure so as to reach a plateau, and be ready for the second operation process.

Case 2

Refer to FIG. 1, about 99 wt % ethanol aqueous solution, as raw material, passes a heat interchanger 1 and then enters a vaporizer 2 for heating and vaporizing by steam, and is heated to 220° C. The heated vapor stream of raw material enters an adsorption tower A from top to bottom through a valve 11. At that time valves 12, 13, 14 and 15 are closed. The adsorption process lasts for 25 seconds. And the heated vapor stream enters an adsorption tower B from top to bottom through a valve 21. At that time valves 22, 23, 24 and 25 are closed. The pressure in tower A and B is set at 2.5 Mpa and adsorption time is set at 50 seconds. Ethanol vapor flows out through valves 15 and 25 from the bottom of the tower. Then it enters the heat interchanger 1 to heat raw ethanol and passes through a cooler 3. After being cooled down, the ethanol product is sampled, and the qualified product containing 99.5 wt % ethanol enters a product storage tank 8 through a valve 51. The unqualified product shall be sent to raw ethanol tank through a valve 52 for re-processing.

After adsorption and dehydration in the adsorption tower A, the valves 13 and 43 are regulated to allow the remaining ethanol vapor gradually flow to the top of tower D through valves 13 and 43. At that time valves 11, 12, 14, 15, 41, 42, 44 and 45 are closed, until the pressures of tower A and tower D are equal, and then an internal circulation is established. In that process, some ethanol vapor is high-concentrated, so it does not have to be pre-processed but enters the tower for adsorption directly. In that case, it can improve the thermal efficiency and reduce equipment investment.

After internal circulation and pressure being balanced, the top of tower A is communicated with a vacuum system 4. Ethanol vapor is sucked out by vacuum draw. A valve 31 of an adsorption tower C is open so as to let the heated ethanol vapor in. Valves 32, 33, 34, 35 are closed. The pressure of the adsorption tower C is 2.5 Mpa, and the adsorption hour is set at 50 seconds. The remaining of the ethanol vapor in tower A is sucked out by vacuum draw and mixed with the ejecting recycling liquid. After enter a recycling liquid tank 6, it turns to a new recycling liquid and is sent into a recycling pump 5. While part of the recycling liquid is sent to a rectifying tower 9 through a valve 53, and enter vaporizer 2 through a valve 55 after rectifying, and then superheat it as raw ethanol vapor. The bottoms of the rectifying tower is pollution-free wastewater. It can be discharged from a valve 54, while the other enters the ejector again as ejecting liquid. The recycling liquid as above-mentioned is ethanol aqueous solution.

Then use the dry alcohol from the tower C which is in a state of adsorption to flow through the molecular sieve in the vacuum tower A from the top to regenerate the molecular sieve after desorption. At that time, valves 33 and 13 are open, while valves 31,32,34,35, 11, 12, 14 and 15 are closed.

Then the pressure of tower A is −0.1 Mpa after regeneration. It is then connected to the adsorption tower B in which adsorption has been completed, to form an internal circulation, and then increase the pressure so as to reach a plateau, and be ready for the second operation process.

Case 3

Refer to FIG. 1, the about 85 wt % ethanol aqueous solution, as raw material, passes a heat interchanger 1 and then enters a vaporizer 2 for heating and vaporizing by steam, and is heated to 150° C. The heated vapor stream of raw material enters an adsorption tower A from top to bottom through a valve 11. At that time valves 12, 13, 14 and 15 are closed. The adsorption process lasts for 125 seconds. And the heated vapor stream enters adsorption tower B from top to bottom through a valve 21. At that time valves 22, 23, 24 and 25 are closed. The pressure in tower A and B is set at 1.0 Mpa. And the adsorption hour is set at 250 seconds. Ethanol vapor flows out through valves 15 and 25 from the bottom of tower. It then enters the heat interchanger 1 to heat raw ethanol and passes through a cooler 3. After being cooled down, the ethanol product is sampled, and the qualified product containing 99.5 wt % ethanol enters a product storage tank 8 through a valve 51. The unqualified product shall be sent to raw ethanol tank through a valve 52 for re-processing.

After adsorption and dehydration in the adsorption tower A, the valves 13 and 43 are regulated to allow let the remaining ethanol vapor gradually flow to the top of tower D through valves 13 and 43. At that time valves 11, 12, 14, 15, 41, 42, 44 and 45 are closed, until the pressures of tower A and tower D are equal, and then an internal circulation is established. In that process, some ethanol vapor is high-concentrated, so it does not have to be pre-processed but enters the tower for adsorption directly. In that case, it can improve the thermal efficiency and reduce the equipment investment.

After internal circulation and pressure being balanced, the top of tower A is communicated with a vacuum system 4. Ethanol vapor is sucked out by vacuum draw. A valve 31 of an adsorption tower C is open so as to let the heated ethanol vapor in. Valves 32, 33, 34, 35 are closed. The pressure of the adsorption tower C is 1.0 Mpa, and the adsorption hour is set at 250 seconds. The remaining of the ethanol vapor in tower A is sucked out by vacuum draw and mixed with the ejecting recycling liquid. After enter recycling liquid tank 6, it turns to a new recycling liquid and is sent into a recycling pump 5. While part of the recycling liquid is sent to a rectifying tower 9 through a valve 53, and enters a vaporizer 2 through a valve 55 after rectifying, and then superheat it as raw ethanol vapor. The bottoms of the rectifying tower is pollution-free wastewater. It can bed discharged from a valve 54, while the other enters the ejector again as ejecting liquid. The recycling liquid as above-mentioned is ethanol aqueous solution.

Then use the dry alcohol from the tower C which is in a state of adsorption to flow through the molecular sieve in the vacuum tower A from the top to regenerate the molecular sieve after desorption. At that time, valves 33 and 13 are open, while valves 31,32,34,35, 11, 12, 14 and 15 are closed.

Then the pressure of tower A is −0.05 Mpa after regeneration. Connect it to the adsorption tower B in which adsorption has finished, to form an internal circulation, and then increase the pressure so as to reach a plateau, and be ready for the second operation process.

What is claimed is:

1. A method of anhydrous ethanol production using internal circulation by alternation of multiple towers comprising the steps of:
   i) allowing a 70-99 wt % ethanol aqueous solution, as raw material, to pass a heat interchanger and then enter a vaporizer for heating and vaporizing by steam to obtain a vapor stream of raw material, and then heating the vapor stream of raw material to 80-220° C.;
   ii) allowing the heated vapor stream of raw material to alternatively enter several adsorption towers which are at adsorption mode in turn from the top thereof for adsorption and dehydration, wherein the pressure of the adsorption towers is 0.1-2.5 MPa and the adsorption process lasts 50-500 seconds; when water concentrations in any one of the adsorption towers is nearly saturated, the feeding of the adsorption tower is stopped; allowing an ethanol stream to flow out from the bottom of the adsorption tower and enter the heat interchanger to heat raw ethanol, and after cooling down by a product cooler, sampling an ethanol product, and entering a qualified product containing 99.5-99.99 wt % ethanol into a product storage tank, sending an unqualified product to a raw ethanol tank for re-processing;
   iii) after adsorption and dehydration, regulating a valve to allow the remaining alcohol in the tower in which adsorption has been finished to gradually flow into the towers at adsorption mode, until their pressures are equal, establishing internal circulation, which is the course of balancing the pressure in the tower in which adsorption has been finished and the towers in adsorption mode;
   iv) after internal circulation and pressure balancing, communicating a top portion of the adsorption tower in which adsorption has been finished with a vacuum system to suck out remaining ethanol stream, which is liquefied after mixing with ejecting recycling liquid and becomes a new recycling liquid to be sent to a recycle pump, sending part of the recycling liquid to a rectifying tower and collecting in the raw ethanol tank as raw material after rectification, wherein the liquid in a bottom portion of the rectifying tower is pollution-free waste water, which can be discharged directly, and entering the remaining recycling liquid into an ejector again as ejecting liquid;
   v) flowing alcohol from an adsorption tower which is in the state of adsorption through a molecular sieve in a vacuum tower from the top to regenerate the molecular sieve after desorption;
   vi) concentrating the tower after regeneration in which the pressure is −0.01-0.1 MPa to another adsorption tower in which adsorption has been completed, to form an internal circulation, and increasing the pressure and performing a second operation process.

2. The method of anhydrous ethanol production using internal circulation by alternation of multiple towers according to claim 1, wherein said recycling liquid is ethanol aqueous solution.

3. The method of anhydrous ethanol production using internal circulation by alternation of multiple towers according to claim 1, wherein the number of said adsorption towers is from four to twelve.

4. The method of anhydrous ethanol production using internal circulation by alternation of multiple towers according to claim 1, wherein the molecular sieve is used as an adsorbent in the adsorption tower.

* * * * *